United States Patent [19]

Lafond

[11] Patent Number: 5,564,829
[45] Date of Patent: Oct. 15, 1996

[54] DISPOSABLE STERILE BAG FOR BLENDERS

[75] Inventor: Danielle Lafond, Beloeil, Canada

[73] Assignee: Labplas Inc., St-Mathieu de Beloeil, Canada

[21] Appl. No.: 437,630

[22] Filed: May 9, 1995

[51] Int. Cl.⁶ .................................................. B01F 3/00
[52] U.S. Cl. ........................... 366/348; 366/69; 383/209
[58] Field of Search .................................. 366/348, 349, 366/69; 383/61, 209; 215/11.3

[56] References Cited

U.S. PATENT DOCUMENTS

| 2,107,851 | 2/1938 | Boehm | 366/69 |
|---|---|---|---|
| 2,539,457 | 1/1951 | Metheny | 366/69 |
| 2,590,462 | 3/1952 | Rassenfoss . | |
| 2,973,131 | 2/1961 | Mead et al. . | |
| 3,189,253 | 6/1965 | Mojonnier . | |
| 3,547,257 | 12/1970 | Armentrout | 383/209 |
| 3,771,773 | 11/1973 | Schriever | 366/69 |
| 4,301,925 | 11/1981 | Bogart . | |
| 4,356,954 | 11/1982 | Mojonnier | 383/61 |
| 4,898,477 | 2/1990 | Cox et al. | 383/209 |
| 5,180,229 | 1/1993 | Niemeyer . | |
| 5,224,779 | 7/1993 | Thompson | 383/209 |

Primary Examiner—Robert W. Jenkins
Attorney, Agent, or Firm—Swabey Ogilvy Renault

[57] ABSTRACT

A disposable sterile plastic bag is proposed for holding samples in blenders during the mixing thereof comprises a two-ply sheet flexible material integrally joined at opposed side edges thereof and joined at the upper and lower ends thereof respectively by upper and lower heat seals with a sealed sample receiving chamber being defined between the two plastic sheets inwardly of the bag's side edges and upper and lower seals. Inwardly of the upper seal, there is defined a tear off line transversally across the two sheets and parallelly to the upper seal thereby forming a detachable strip outwardly of the tear off line. When the sample is ready to be introduced in the bag, the strip is removed from the bag by pulling it so as to cause rupture of the two sheets at the tear off line. The bag's chamber is thus sterile when the sample is introduced therein and the bag and its contents can then be inserted in the blender. The bag's sterility does not depend on how the bag is package or on the integrity of the packaging's seal as the bag is itself sterile until the strip is removed therefrom, that is until the bag is ready to be used.

7 Claims, 2 Drawing Sheets

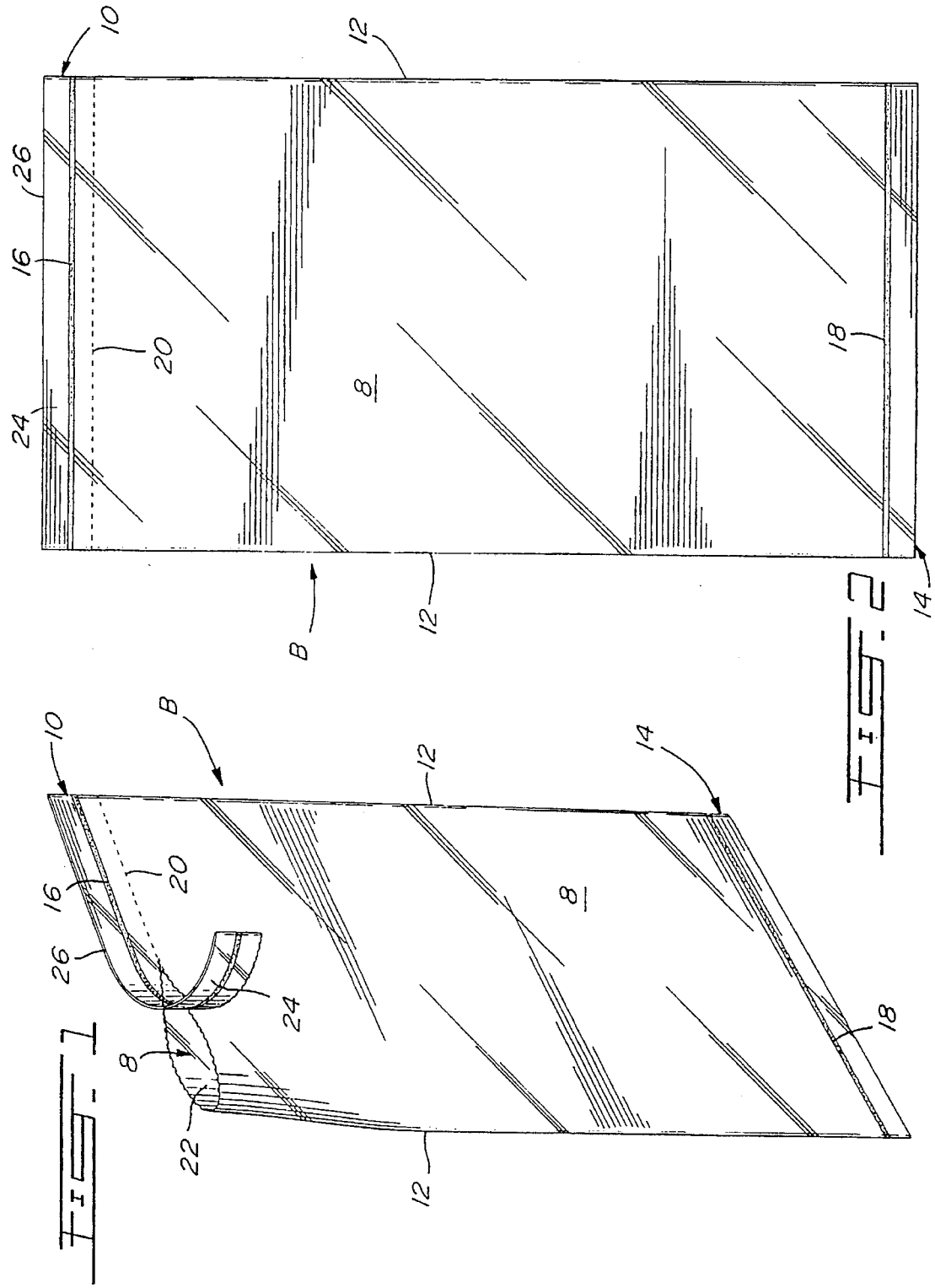

DISPOSABLE STERILE BAG FOR BLENDERS

BACKGROUND OF THE INVENTION

1. Field of the Invention

The present invention relates to sterile plastics bags for use in handling clinical samples and the like and, more particularly, to a sterile plastic bag for holding samples in blenders used in laboratories, in hospitals, in the food industry, etc.

2. Description of the Prior Art

Various bags have been developed for the sterile transportation and/or storage of samples in the medical and food fields, such as human fluid samples, milk, water in environmental studies, etc. Such plastic bags may include near an open end thereof a wire or metal strip which is mounted transversely across the bag with ends extending past the side edges of the bag. Once the bag has been filled with the sample to be transported/stored, the open end is folded at least once over the bag about the wire or metal strip so as to close the open end and the ends of the wire or metal strip are then folded at the side edges of the bag and brought around so as to extend inwardly behind the bag. This safely and effectively encloses the sample in the plastic bag.

In other applications, sterile plastic bags are required for use in electro-mechanical equipment or machines for various purposes. For instance, samples must often be mixed such in laboratories, in hospitals and in the food industry, and this is carried out by way of blenders which are adapted to receive therein the sterile plastic bag into which the sample to be mixed has been introduced.

Obviously, the sterility of the bags used in such blenders is of utmost importance in order to prevent the sample from being contaminated. The conventional bags used with the blenders are simple plastic two-ply bags having a lower end thereof closed by heat sealing and both side edges thereof closed either by heat sealing or integrally if the bag was made from an elongated tubular sleeve transversally cut so that its longitudinal length corresponds to the height of the intended bag, that is to the length of the bag's side edges. Previously, the sterility of these bags was ensured by packaging the in the bags in a sterile closed pouch. On the other hand, once the pouch's seal was broken so that one or more bags could be retrieved for use in the blenders, the integrity of the sterility of the remaining bags in the pouch was compromised to a point that, depending on the bags' applications, the remaining bags were often thrown away to prevent the subsequent use of potentially non sterile bags.

SUMMARY OF THE INVENTION

It is therefore an aim of the present invention to provide a novel sterile bag for holding therein samples for use in blenders or the like.

It is also aim of the present invention to provide a novel sterile bag wherein each individual bag's sterility is ensured by a sealing system provided on each bag.

It is a further aim of the present invention to provide a novel method of using a sterile bag containing a sample in conjunction with a blender, or the like, adapted to receive therein the bag and its contents for the subsequent blending or mixing of such contents.

Therefore, in accordance with the present invention, there is provided a disposable sterile plastic bag for holding samples or the like for use in machines such as blenders and homogenizers, comprising flexible closed enclosure means defining chamber means adapted to contain therein a sample to be mixed in the blender or homogenizer, said enclosure means being permanently sealed except at one portion thereof which comprises bag access means adapted to substantially seal said bag in a first position thereof but also adapted to selectively allow in a second position thereof the sample to be introduced in said chamber means when it is desired to use said bag.

In a specific construction, said access means comprise detachable strip means including sealing means for sealing said bag in said first position but adapted to be removed from said bag with said detachable strip means in said second position thereby opening said bag at said one portion thereof for subsequent receipt of the sample therein.

In another specific construction, said enclosure means comprise front and rear rectangular sheet means joined at opposed side edges thereof and at a bottom end thereof, said strip means being provided at an upper end of said sheet means for substantially sealing in said first position said chamber means defined between said sheet means, said strip means comprising a tear off line extending inwardly of said sealing means, whereby in said second position said strip means is detached from said upper end of said enclosure means at said tear off line with said sealing means being removed therefrom with said strip means thereby allowing access to said chamber means.

Also in accordance with the present invention, there is provided a disposable sterile bag in combination with a mixing device, said bag being adapted to contain samples or the like and to be inserted in said mixing device, said mixing device being adapted for mixing the sample contained in said bag, said bag comprising flexible closed enclosure means defining chamber means adapted to contain therein the sample to be mixed in said mixing device, said enclosure means being permanently sealed except at one portion thereof which comprises bag access means adapted to substantially seal said bag in a first position thereof but also adapted to selectively allow in a second position thereof the sample to be introduced in said chamber means when it is desired to use said bag, whereby once in said second position the sample can be received in said bag with said bag and the sample contained therein being then inserted in said mixing device.

Further in accordance with the present invention, there is provided a method of mixing sterile samples in mixing devices such as blenders and homogenizers, comprising the steps of:

a) providing a disposable sterile bag comprising flexible closed enclosure means defining chamber means adapted to contain therein a sample to be mixed in the mixing device, said enclosure means being permanently sealed except at one initially sealed portion thereof which comprises bag access means substantially sealing said bag in a first position thereof but also adapted to selectively allow in a second position thereof the sample to be introduced in said chamber means when it is desired to use said bag;

b) handling said bag access means from said first to said second position thereof;

c) introducing the sample in said chamber means by way of said bag access means in said second position thereof; and d) inserting said bag and the sample contained therein in said mixing device; and e) operating said mixing device for causing the sample to be mixed in said bag.

In a specific method, after step c) and before step e) said bag is closed at said access means for isolating the sample in said bag.

In another specific method, said access means comprise detachable strip means including sealing means for sealing said bag in said first position in step a); but adapted in step b) to be removed from said bag along with said detachable strip means in said second position thereby opening said bag at said one portion thereof for subsequent receipt in step c) of the sample therein.

In a still more specific method, said enclosure means comprise front and rear rectangular sheet means joined at opposed side edges thereof and at a bottom end thereof, said strip means being provided at an upper end of said sheet means for substantially sealing in step a) said chamber means defined between said sheet means, said strip means comprising a tear off line extending inwardly of said sealing means, whereby in step b) said strip means is detached from said upper end of said enclosure means at said tear off line with said sealing means being removed therefrom with said strip means thereby allowing access to said chamber means.

BRIEF DESCRIPTION OF THE DRAWINGS

Having thus generally described the nature of the invention, reference will now be made to the accompanying drawings, showing by way of illustration a preferred embodiment thereof, and in which:

FIG. 1 is a perspective view of a sterile plastic bag in accordance with the present invention adapted to hold therein samples and for use in blenders for mixing the samples, wherein the sterile bag is shown in a partly open position; and FIG. 2 is an elevational view of the sterile bag of the present invention in an unused sealed.

DESCRIPTION OF THE PREFERRED EMBODIMENTS

Figure 3:
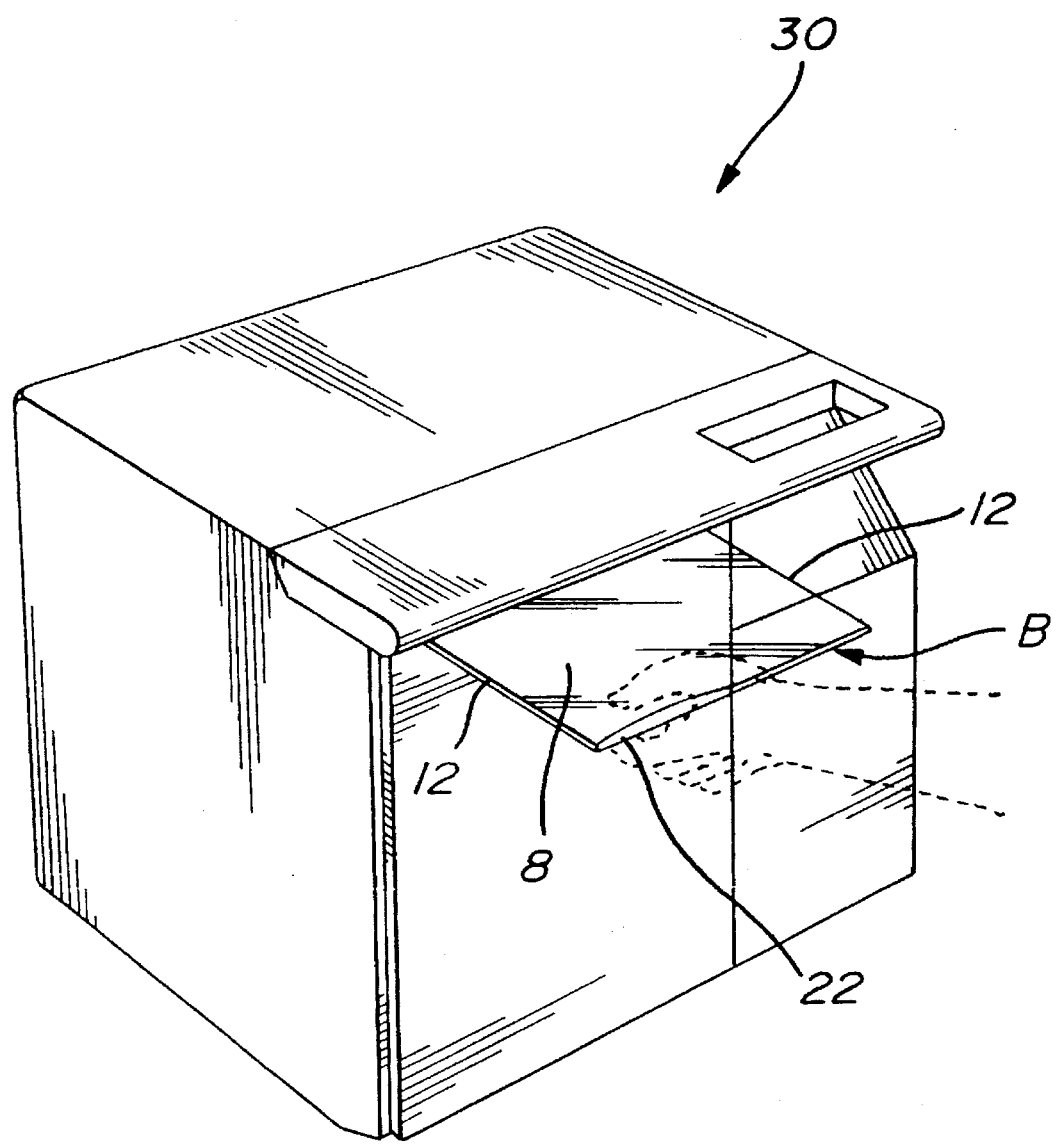
FIG. 3 is a perspective view of a blender, or the like, shown with bag of the present invention received therein for mixing the contents of the plastic bag.

FIG. 1 illustrates a sterile plastic bag B in accordance with the present invention which is made for instance from heavy-gauge transparent polyethylene. More particularly, the bag B can be made from an elongated sleeve which is transversely cut so as to obtain a bag of desired length or height, that is the distance between the opposed open ends of the severed sleeve. Such a construction produces a bag having no side seams which reduces the costs of manufacture of the bag B and increases the efficiency of the protection afforded by the bag B. Then, the bottom end of the severed sleeve is closed, for example, by heat sealing thereby producing a bag having an open upper end. This upper end, in the present invention, is temporarily sealed by a further heat seal which is carried out between the upper edge of the bag and a tear off line defined transversely across the bag at its upper end, whereby when the bag is required for holding a sample for subsequent use in a blender, the tear off strip defined between the tear off line and the upper edge of the bag can be detached from the latter. With this construction, the bag remains substantially and sufficiently sterile until it is used, that is until the tear off strip is removed therefrom.

With reference to the enclosed drawings, the plastic bag B is shown in FIG. 2 in a sealed position thereof and is produced and sold as such. When a sample or the like must be deposited in the bag B for subsequent purposes in a blender, the bag is opened by proceeding as illustrated in FIG. 1.

The bag B is of the two-ply type having identical front and rear sheets 8 integrally joined at side edges 12 thereof and having opposite upper and lower ends 10 and 14, respectively. The two sheets 8 are joined in a tight sealed manner at the upper end 10 of the bag B by known connection means, such as a heat seal 16. Similarly, the sheets 8 are sealingly joined at the lower end 14 of the bag B by a lower heat seal 18.

A tear off line 20 is punctured through both sheets 8 across the upper end 10 of the bag B and lower than the upper heat seal 16 such that the upper heat seal 16 extends substantially parallelly between the tear off line 20 and an upper edge 26 of the bag B. Therefore, there is a tear off strip 24 defined at the upper end 10 of the bag B which when detached from the remainder of the bag B in a manner initiated in FIG. 1, reveals an open mouth 22 of the bag B through which the bag B can obviously be filled with the sample intended to be agitated by the blender, such as blender 30 of FIG. 3.

The present invention is thus very useful to provided simple, economical and sterile sampling bags having a stand-alone sterility which was not offered by conventional bags used in blenders. Indeed, the sterility of the present bag B is not the result as in the prior art of being contained in a sealed pouch along with other bags but is the consequence of the present bag's stand-alone sterility as the bag B in its state shown in FIG. 2 is sterile although not enclosed in a sealed packaging pouch.

The present bag can be used for instance in the Stomacher® Lab Blender which a well-known blender/homogenizer having its trademark registered in the name of Seward Medical, Ltd. The Stomacher® blender provides a rapid, clean and safe blending of samples with the samples never directly contacting the machine as the mixing is achieved with the samples being contained in a sturdy and disposable plastic bag of the conventional type described hereinabove. In operation, the bag, such a conventional bag or the bag B of the present invention, is tightly clamped in the blender 30, as seen in FIG. 3 to prevent any aerosol release. These bags can be heat sealed with the samples being contained therein in order to completely isolate the samples. There is thus no need to clean-up or sterilize blender cups and blades as the bags are simply discarded after use. The Stomacher® blender and others of the same type can be used in food microbiology applications for bacterial counts in food samples and damage to microbial cells and temperature rise are minimal. The Stomacher® blender can also be used in biomedical research applications for bacterial and viral studies, in industrial applications for sterility control of pharmaceutical preparations, creams, ointments, etc., in clinical applications for speeding up the digestion and removal of organisms from sputum and for removing organisms from swabs, tissue biopsy and fecal samples. It is found to be equivalent to glass tissue grinders, and to be excellent for toxicology work such as drug recovery from tissues. There are no sample cross contamination with the Stomacher® blender and its plastics bags B.

Therefore, the blender 30 is of great use but requires disposable plastic bags which are sterile. The present bag B is ideal as it is characterized by stand-alone sterility which does not depend on a sterile packaging.

I claim:

1. A disposable sterile bag in combination with a mixing device, said bag being adapted to contain samples or the like and to be inserted in said mixing device, said mixing device being adapted for mixing the sample contained in said bag, said bag comprising flexible closed enclosure means defining chamber means adapted to contain therein the sample to be mixed in said mixing device, said enclosure means being permanently sealed except at one portion thereof which comprises bag access means adapted to substantially seal said bag in a first position thereof but also adapted to selectively allow in a second position thereof the sample to be introduced in said chamber means when it is desired to use said bag, whereby once in said second position the sample can be received in said bag with said bag and the sample contained therein being then inserted in said mixing device.

2. A disposable sterile bag in combination with a mixing device as defined in claim 1 wherein said access means comprise detachable strip means including sealing means for sealing said bag in said first position but adapted to be removed from said bag with said detachable strip means in said second position thereby opening said bag at said one portion thereof for subsequent receipt of the sample therein.

3. A disposable sterile bag in combination with a mixing device as defined in claim 2, wherein said enclosure means comprise front and rear rectangular sheet means joined at opposed side edges thereof and at a bottom end thereof, said strip means being provided at an upper end of said sheet means for substantially sealing in said first position said chamber means defined between said sheet means, said strip means comprising a tear off line extending inwardly of said sealing means, whereby in said second position said strip means is detached from said upper end of said enclosure means at said tear off line with said sealing means being removed therefrom with said strip means thereby allowing access to said chamber means.

4. A method of mixing sterile samples in mixing devices such as blenders and homogenizers, comprising the steps of:

a) providing a disposable sterile bag comprising flexible closed enclosure means defining chamber means adapted to contain therein a sample to be mixed in the mixing device, said enclosure means being permanently sealed except at one initially sealed portion thereof which comprises bag access means substantially sealing said bag in a first position thereof but also adapted to selectively allow in a second position thereof the sample to be introduced in said chamber means when it is desired to use said bag;

b) handling said bag access means from said first to said second position thereof;

c) introducing the sample in said chamber means by way of said bag access means in said second position thereof; and d) inserting said bag and the sample contained therein in said mixing device; and e) operating said mixing device for causing the sample to be mixed in said bag.

5. A method as defined in claim 4, wherein after step c) and before step e) said bag is closed at said access means for isolating the sample in said bag.

6. A method as defined in claim 4, wherein said access means comprise detachable strip means including sealing means for sealing said bag in said first position in step a); but adapted in step b) to be removed from said bag along with said detachable strip means in said second position thereby opening said bag at said one portion thereof for subsequent receipt in step c) of the sample therein.

7. A method as defined in claim 6, wherein said enclosure means comprise front and rear rectangular sheet means joined at opposed side edges thereof and at a bottom end thereof, said strip means being provided at an upper end of said sheet means for substantially sealing in step a) said chamber means defined between said sheet means, said strip means comprising a tear off line extending inwardly of said sealing means, whereby in step b) said strip means is detached from said upper end of said enclosure means at said tear off line with said sealing means being removed therefrom with said strip means thereby allowing access to said chamber means.

* * * * *

UNITED STATES PATENT AND TRADEMARK OFFICE
CERTIFICATE OF CORRECTION

PATENT NO : 5,564,829
DATED : October 15, 1996
INVENTOR(S): Danielle Lafond

It is certified that error appears in the above-identified patent and that said Letters Patent is hereby corrected as shown below:

In column 3, line 39, delete"." and insert --position thereof; and--.

In column 3, line 41, after "with" insert --the plastic--.

Signed and Sealed this

Thirtieth Day of May, 2000

Attest:

Q. TODD DICKINSON

Attesting Officer

Director of Patents and Trademarks